(12) United States Patent
Muranjan et al.

(10) Patent No.: US 9,978,165 B2
(45) Date of Patent: May 22, 2018

(54) DYNAMIC PRESENTATION OF WAVEFORM TRACINGS IN A CENTRAL MONITOR PERSPECTIVE

(75) Inventors: Samir Muranjan, Overland Park, KS (US); James Alexander Moseley, Independence, MO (US); Gregory James Kuttenkuler, Shawnee, KS (US); Mark R. Inman, Olathe, KS (US); Jill Ann Meier, Liberty, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 237 days.

(21) Appl. No.: 13/562,447

(22) Filed: Jul. 31, 2012

(65) Prior Publication Data

US 2014/0035925 A1 Feb. 6, 2014

(51) Int. Cl.
*G06T 11/60* (2006.01)
*A61B 5/00* (2006.01)

(52) U.S. Cl.
CPC ........... *G06T 11/60* (2013.01); *G16H 40/63* (2018.01); *A61B 5/0002* (2013.01); *A61B 5/7435* (2013.01)

(58) Field of Classification Search
USPC ...................................................... 345/440.1
See application file for complete search history.

(56) References Cited

U.S. PATENT DOCUMENTS

| | | | |
|---|---|---|---|
| 6,544,173 B2 * | 4/2003 | West | A61B 5/1113 128/903 |
| 2003/0208128 A1 * | 11/2003 | Hamilton et al. | 600/509 |
| 2004/0051721 A1 * | 3/2004 | Ramseth | G06F 19/3406 345/689 |
| 2005/0234687 A1 * | 10/2005 | Sakairi et al. | 703/2 |
| 2009/0153560 A1 * | 6/2009 | Gilbert | G09G 5/00 345/441 |
| 2009/0171169 A1 * | 7/2009 | Nagata | 600/301 |
| 2010/0121157 A1 * | 5/2010 | Espina et al. | 600/301 |
| 2010/0268124 A1 * | 10/2010 | Hamilton et al. | 600/588 |
| 2011/0071414 A1 * | 3/2011 | Heil et al. | 600/511 |
| 2012/0026119 A1 * | 2/2012 | Judy et al. | 345/173 |
| 2012/0075103 A1 * | 3/2012 | Powell et al. | 340/573.1 |
| 2012/0182301 A1 * | 7/2012 | Wenholz | A61B 5/044 345/440.1 |

OTHER PUBLICATIONS

English Machine Translation of WO2012085762 A2.*

* cited by examiner

*Primary Examiner* — Barry Drennan
*Assistant Examiner* — Terrell Robinson
(74) *Attorney, Agent, or Firm* — Shook, Hardy & Bacon L.L.P.

(57) ABSTRACT

Methods, computer systems, and computer storage media are provided for automatically populating a central monitor perspective with waveform tracings having a predetermined aspect ratio. A selection of a unit location is received, and monitoring devices connected to patients at the unit location are detected. Waveform tracings associated with the active monitoring devices are presented in a predetermined aspect ratio in the central monitor perspective. As new monitoring devices are connected to patients, or as monitoring devices are disconnected from patients, the central monitor perspective is automatically refreshed to reflect currently active waveform tracings having the predetermined aspect ratio.

20 Claims, 8 Drawing Sheets

DYNAMIC PRESENTATION OF WAVEFORM TRACINGS IN A CENTRAL MONITOR PERSPECTIVE

BACKGROUND

Some medical monitoring devices produce waveform tracings. Such monitoring devices include fetal heart rate monitors, uterine contraction monitors, blood pressure monitors, respiratory monitors, heart rhythm monitors, and the like. These waveform tracings may be presented on a display device associated with, for example, a central location such as a nursing unit at a healthcare facility. In some instances, the display device may present multiple waveform tracings associated with different patients on the unit. Currently, multiple waveform tracings are not presented in such a way as to effectively utilize all of the available display space on the display device. Instead, the multiple waveform tracings may be displayed in one small area of the display screen, and the rest of the display screen is left blank in anticipation of additional waveform tracings needing to be displayed.

Another problem with the current system is that when a new patient is admitted to the unit and is connected to a monitoring device, a caregiver must manually select the patient on the display device to initiate the presentation of the waveform tracing associated with the monitoring device. Likewise, when a patient is no longer connected to a monitoring device, the caregiver must manually de-select the patient on the display device to remove information associated with the monitoring device.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer storage media for automatically populating a central monitor perspective with waveform tracing information and maintaining a predetermined aspect ratio associated with the waveform tracings. Monitoring devices connected to patients at a unit location are detected, and waveform tracings associated with the monitoring devices are automatically presented in the central monitor perspective in such a way as to effectively utilize the available screen real estate of the central monitor perspective. As new monitoring devices are connected to patients, or as monitoring devices are disconnected from patients, the central monitor perspective is automatically refreshed to reflect currently active waveform tracings having the predetermined aspect ratio. The aspect ratio is configured to enable clinicians to quickly identify if the waveform tracings are within normal limits.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer storage media for automatically populating a central monitor perspective with waveform tracing information and maintaining a predetermined aspect ratio associated with the waveform tracings. Monitoring devices connected to patients at a unit location are detected, and waveform tracings associated with the monitoring devices are automatically presented in the central monitor perspective in such a way as to effectively utilize the available screen real estate of the central monitor perspective. As new monitoring devices are connected to patients, or as monitoring devices are disconnected from patients, the central monitor perspective is automatically refreshed to reflect currently active waveform tracings having the predetermined aspect ratio. The aspect ratio is configured to enable clinicians to quickly identify if the waveform tracings are within normal limits.

Figure 1:
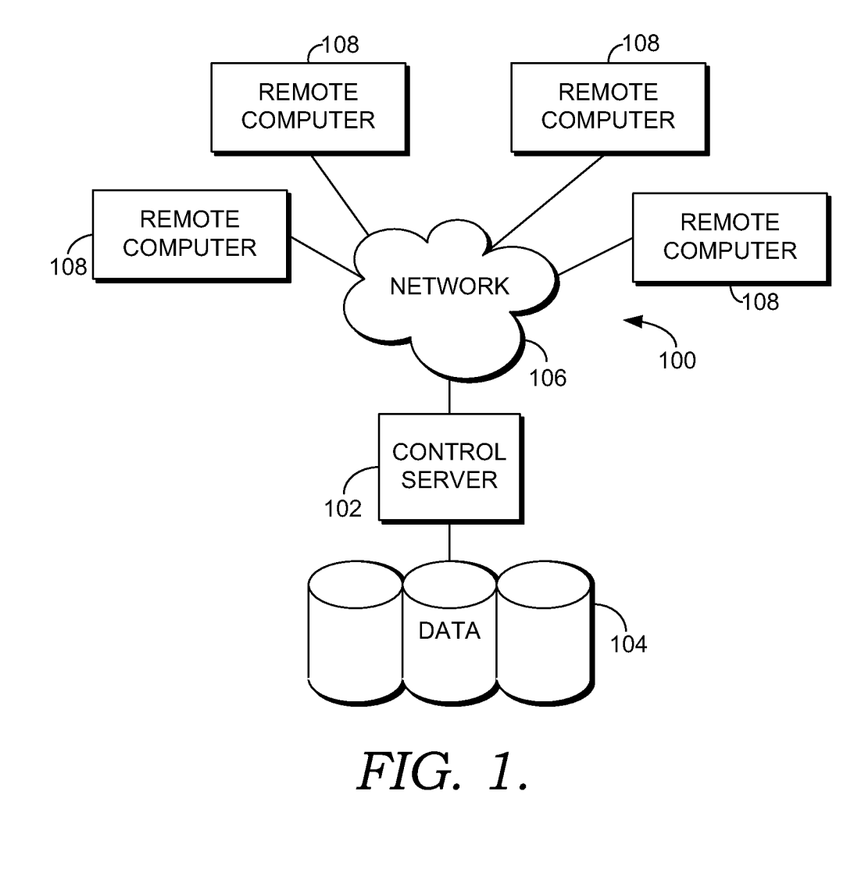
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multi-processor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
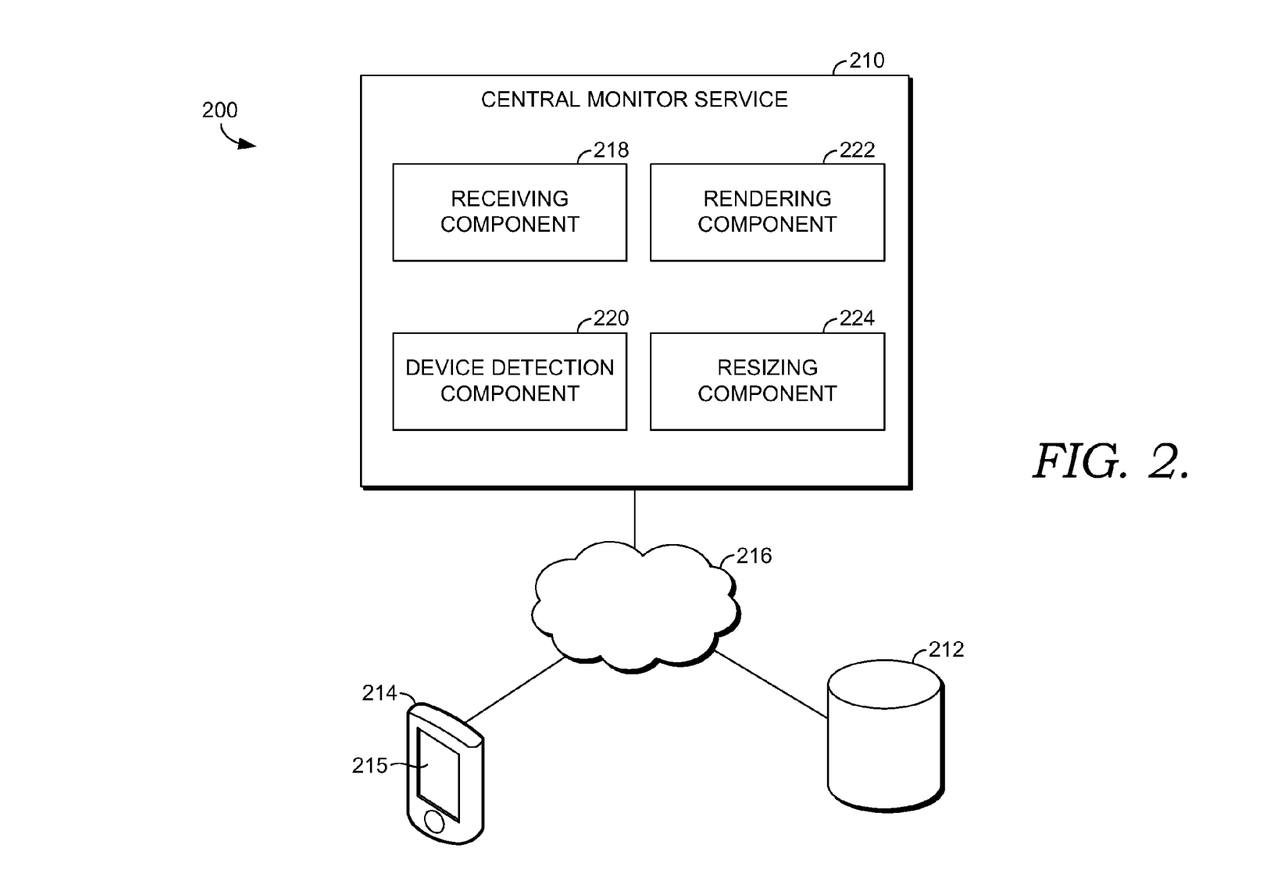
FIG. 2 is a block diagram of an exemplary system for automatically populating a central monitor perspective with waveform tracings suitable to implement embodiments of the present invention.

Turning now to FIG. 2, an exemplary computing system environment 200 is depicted suitable for use in implementing embodiments of the present invention. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes a central monitor service 210, a data store 212, and an end-user computing device 214 with a display screen 215 all in communication with one another via a network 216. The network 216 may include, without limitation, one or more local area networks (LANs) and/or wide area networks (WANs). Such networking environments are commonplace in offices, enterprise-wide computer networks, intranets and the Internet. Accordingly, the network 216 is not further described herein.

In some embodiments, one or more of the illustrated components/modules may be implemented as stand-alone applications. In other embodiments, one or more of the illustrated components/modules may be integrated directly into the operating system of the central monitor service 210. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the central monitor service 210 might reside on a server, cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The data store 212 is configured to store information for use by, for example, the central monitor service 210. The information stored in association with the data store 212 is configured to be searchable for one or more items of information stored in association therewith. The information stored in association with the data store 212 may comprise general information used by the central monitor service 210.

The data store 212 may store electronic medical records (EMRs) of patients associated with one or more healthcare facilities. EMRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

The content and volume of such information in the data store 212 are not intended to limit the scope of embodiments of the present invention in any way. Further, though illustrated as a single, independent component, the data store 212 may, in fact, be a plurality of storage devices, for instance, a database cluster, portions of which may reside on the central monitor service 210, the end-user computing device 214, and/or any combination thereof.

As shown, the end-user computing device 214 includes a display screen 215. The display screen 215 is configured to present information to the user of the end-user computing device 214, for instance, information relevant to communications initiated by and/or received by the end-user computing device 214, waveform tracings, patient information, vital signs information, and the like. The display screen 215 may be located in a central location such as a nursing station or clinician station associated with a unit at a healthcare facility. Nursing or clinician stations are generally designed to provide care to one or more patients who are located in the healthcare facility unit. Thus, the display screen 215 may be configured to present information associated with patients located in the unit to caregivers at the nursing or clinician station. Further, the display screen 215 may comprise one display screen or multiple display screens. Embodiments are not intended to be limited to visual display but rather may also include audio presentation, combined audio/visual presentation, and the like.

Components of the central monitor service 210 may include a processing unit, internal system memory, and a suitable system bus for coupling various system components, including one or more data stores for storing information (e.g., files and metadata associated therewith). The central monitor service 210 typically includes, or has access to, a variety of computer-readable media.

The computing system environment 200 is merely exemplary. While the central monitor service 210 is illustrated as a single unit, it will be appreciated that the central monitor service 210 is scalable. For example, the central monitor service 210 may in actuality include a plurality of computing devices in communication with one another. Moreover, the data store 212, or portions thereof, may be included within, for instance, the central monitor service 210 as a computer-storage medium. The single unit depictions are meant for clarity, not to limit the scope of embodiments in any form.

As shown in FIG. 2, the central monitor service 210 comprises a receiving component 218, a device detection component 220, a rendering component 222, and a resizing component 224. In some embodiments, one or more of the components 218, 220, 222, and 224 may be implemented as stand-alone applications. In other embodiments, one or more of the components 218, 220, 222, and 224 may be integrated directly into the operating system of a computing device such as the remote computer 108 of FIG. 1. It will be understood that the components 218, 220, 222, and 224 illustrated in FIG. 2 are exemplary in nature and in number and should not be construed as limiting. Any number of components may be employed to achieve the desired functionality within the scope of embodiments hereof.

The receiving component 218 is configured to receive user selections, inputs, and/or requests from a computing device associated with, for example, a healthcare facility. A selection may include a unit or station location, such as a nursing unit location, to present in a central monitor perspective on a display device such as, for example, the display screen 215. Exemplary unit locations may include labor and delivery units, emergency room units, telemetry units, post-surgery recovery units, pre-surgery units, intensive care units, and the like. Each of these units is capable of caring for a number of patients located in that unit.

The device detection component 220 is configured to detect if a monitoring device is connected to a patient in the selected unit location, the type of monitoring device connected to the patient in the selected unit location, and whether the device has been electronically associated with the patient. The device detection component 220 is configured to detect multiple, different kinds of devices. For example, the device detection component 220 may be configured to detect fetal monitoring devices, respiratory monitoring devices, blood pressure monitoring devices, hearth rhythm monitoring devices, and the like. The device detection component 220 is also configured to determine a location of the monitoring device and whether the central monitor service 210 is monitoring that location.

The device detection component 220 is further configured to detect when a monitoring device is actively monitoring a patient (i.e., is "online") and to detect when a monitoring device is no longer actively monitoring a patient (i.e., is "offline"). A monitoring device may actively monitor a patient without the monitoring device being electronically associated with the patient. Using patients in a labor and delivery unit (LDU) as an example, LDU patients typically have episodes where they are being actively monitored without being electronically associated with the monitoring device. For instance, a patient in early labor may be connected to a monitoring device for a brief period while resting or being examined, but be disconnected from the monitoring device while the patient walks the hallways in an attempt to augment the labor process. As well, a patient may be monitored for a brief period of time to determine if the patient is actually in labor. If the patient is not in labor, monitoring ceases and the patient is sent home. In yet another example, a patient in an emergency situation may be monitored without being electronically associated with the monitoring device. Other scenarios involving intermittent monitoring are contemplated as being within the scope of the invention (e.g., EKG monitoring, EEG monitoring, blood pressure monitoring, and the like).

Additionally, the device detection component 220 is configured to determine if a monitoring device has been electronically associated with a patient. A monitoring device may be electronically associated with a patient using patient identification information such as name, gender, date of birth, identification number, and the like. Any waveform tracings from a monitoring device that has been electronically associated with a patient will have the patient identification information associated with the waveform tracing; this patient identification information may be presented in conjunction with the waveform tracing.

The rendering component 222 is configured to render real-time and historical waveform tracings associated with the monitoring devices in a central monitoring perspective on a display device. The waveform tracings are displayed by plotting a characteristic of the waveform on the y-axis against time on the x-axis. The waveform tracings may be presented with a predetermined aspect ratio that mimics the aspect ratio of traditional hard copies of waveform tracings. This facilitates clinician decision making as the clinicians can quickly determine whether the waveform tracing is within normal limits without having to account for an unfamiliar aspect ratio. In one aspect, the predetermined aspect ratio comprises a ratio of 1 minute on the x-axis of the waveform tracing to 24% of the height of the y-axis—this is expressed as a 1:24 ratio. Other exemplary ratios may include 1:20, 1:21, 1:22, 1:23, or any aspect ratio between these values.

In another aspect of the invention, the user can choose to limit each waveform to, for example, 60 minutes of tracings regardless of the resulting size or aspect ratio of the waveform tracing. In this aspect, a predetermined aspect ratio is not necessarily maintained, and the central monitor perspective displays 60 minutes of waveform tracings in each cell. Although the example uses 60 minutes of waveform tracings, the user can select time values of any range.

If a monitoring device has been electronically associated with a patient, the rendering component 222 is configured to present patient identification information in association with the waveform tracing. Patient identification information may include patient name, age, gender, patient identification number, and the like. If a monitoring device is actively monitoring a patient but has not been electronically associated with the patient, the rendering component 222 is configured present a name associated with the monitoring device. The name may include a unit location identifier in combination with a device number identifier. In one aspect, if a monitoring device is electronically associated with a patient while the monitoring device's associated waveform tracing is being presented, the patient identification information is automatically populated in the central monitor perspective.

The rendering component 222 is further configured to present vital signs in conjunction with a waveform tracing. For instance, a numerical value associated with a heart rate, a respiratory rate, or a blood pressure may be presented in association with a waveform tracing. The rendering component 222 may also present alerts and/or notifications if it is determined that the waveform tracings and/or vital signs are outside the normal limits.

The rendering component 222 may present each waveform tracing in a separate "cell" in the central monitor perspective. The term "cell" is not meant to be taken literally, but, instead, is meant to imply a defined space of certain proportions. The cells are sized to substantially occupy the available real estate in the central monitor perspective leaving a minimal amount of unused space. In one aspect, the rendering component 222 is configured to present a maximum of 25 waveform tracings in 25 separate cells. The 25 separate cells may be arranged in a 5×5 grid although other grid arrangements are contemplated.

The resizing component 224 is configured to automatically resize the real-time waveform tracings based on the number of active monitoring devices while maintaining the predetermined aspect ratio of the waveform tracings. The tracings may be resized upward or downward depending on whether a new active monitoring device is detected or an existing monitoring device is disconnected. For instance, the device detection component 220 may detect that a monitoring device has come online. The waveform tracing associated with this monitoring device is automatically presented in the central monitor perspective. Any existing waveform tracings are downsized appropriately to make room for the new waveform tracing. Both the new waveform tracing and any existing waveform tracings are presented with the predetermined aspect ratio. Further, both the new waveform tracing and any existing waveform tracings are presented in similar-sized cells. In another example, the device detection component 220 may detect that a monitoring device has gone offline (i.e., is no longer actively monitoring a patient). The waveform tracing associated with that monitoring device is automatically removed from the central monitor perspective, and the remaining waveform tracings are resized upward while maintaining the predetermined aspect ratio.

Figure 3:
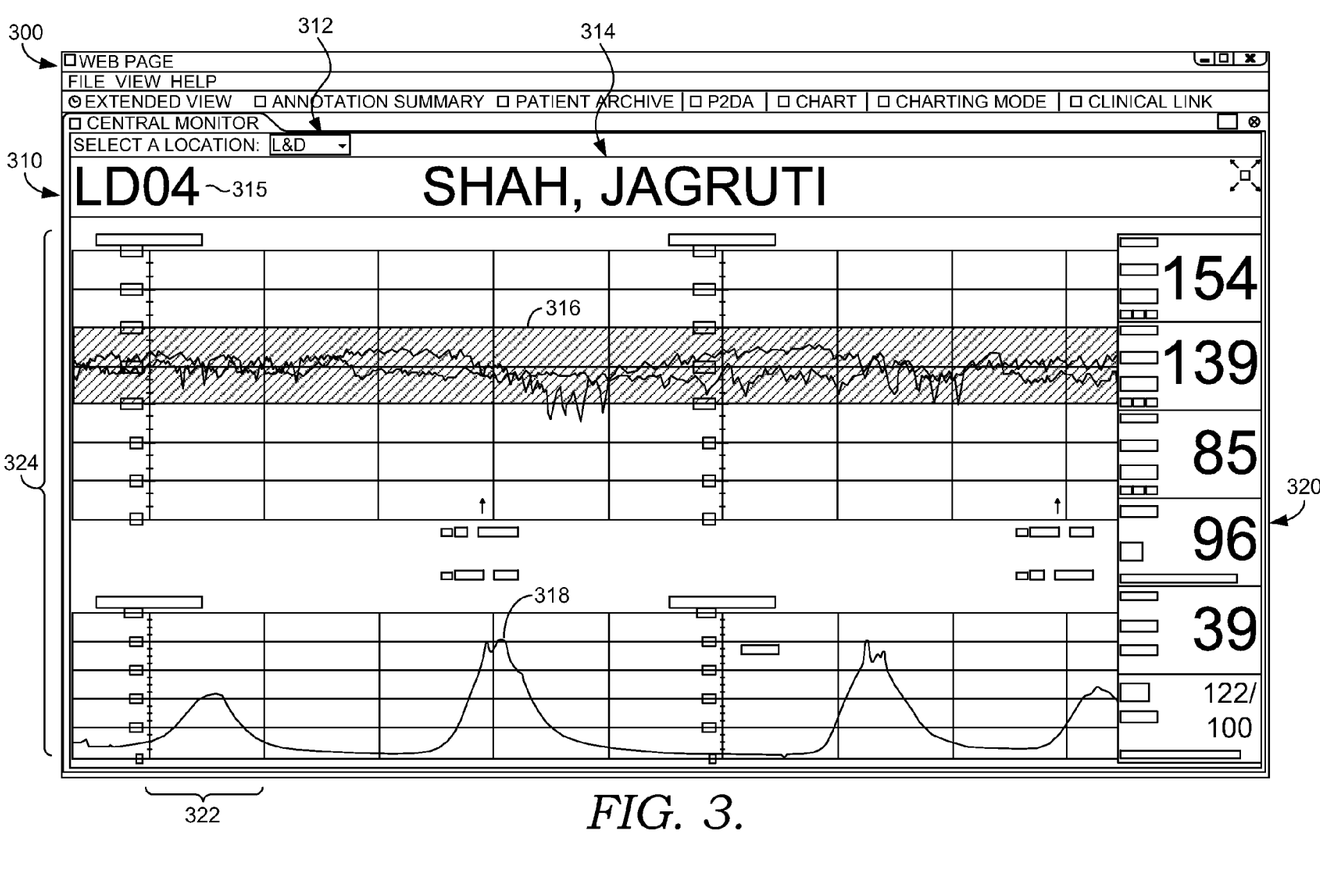
FIGS. 3-7 are exemplary views of a central monitor perspective presenting one or multiple waveform tracings in accordance with embodiments of the present invention.

FIGS. 3-7 depict exemplary views of a central monitor perspective presenting one or more waveform tracings. FIG. 3 depicts a central monitor perspective 300 presenting a single waveform tracing in a waveform tracing cell 310. As can be seen, the waveform tracing cell 310 substantially occupies the majority of the available screen space of the central monitor perspective 300. At the top portion of the central monitor perspective 300, a location display area 312 presents available unit locations using, for example, a drop down list. A user is able to select a location to present in the central monitor perspective 300. Available locations may include different units within a healthcare facility such as a labor and delivery unit, an emergency room unit, an intensive care unit, a telemetry unit, a pre- or post-surgical unit, and the like. Each of these units may have one or more centrally-located display devices for displaying a central monitor perspective.

The waveform tracing cell 310 includes a patient name 314. The patient name 314 is presented in association with the waveform tracing cell 310 if the patient has been electronically associated with a monitoring device that is outputting the waveform information. The waveform tracing cell 310 also includes a device name 315. The device name 315 may include a location identifier as well as a device number identifier. In this case the device name 315 is LD04 indicating that fetal monitoring device 04 is located in the labor and delivery unit.

The waveform tracing cell 310 further includes a uterine contraction waveform tracing 318 and a fetal heart rate waveform tracing 316. The uterine contraction waveform tracing 318 and the fetal heart rate waveform tracing 316 may be captured by a single monitoring device or by multiple monitoring devices aggregated under a single device name. Although not shown, the waveform tracing cell 310 may include multiple fetal heart rate waveform tracings if the mother is pregnant with twins, triplets, etc.

The waveform tracing cell 310 may include a vital signs display area 320 that displays one or more vital signs associated with the waveform tracing cell 310 such as, for example, fetal heart rate, maternal heart rate, maternal blood pressure, maternal respiratory rate, uterine contraction strength, and the like. The vital signs display area 320 may not be presented when the number of different waveform tracing cells presented exceeds a predetermined number such as, for example, 8, 9 or 10 different waveform tracing cells.

The waveform tracing cell 310 has an x-axis dimension and a y-axis dimension; the x-axis represents time and the y-axis represents numerical values associated with one or more monitoring devices (e.g., heart rate, uterine contraction strength, etc.). In one aspect, the predetermined aspect ratio comprises an x to y ratio of one minute along the x-axis (represented by distance 322) to 24% of the height of the waveform tracing cell 310 (represented by height 324). Other exemplary aspect ratios may include 1:20, 1:21, 1:22, 1:23 and any aspect ratio between these figures.

Figure 4:
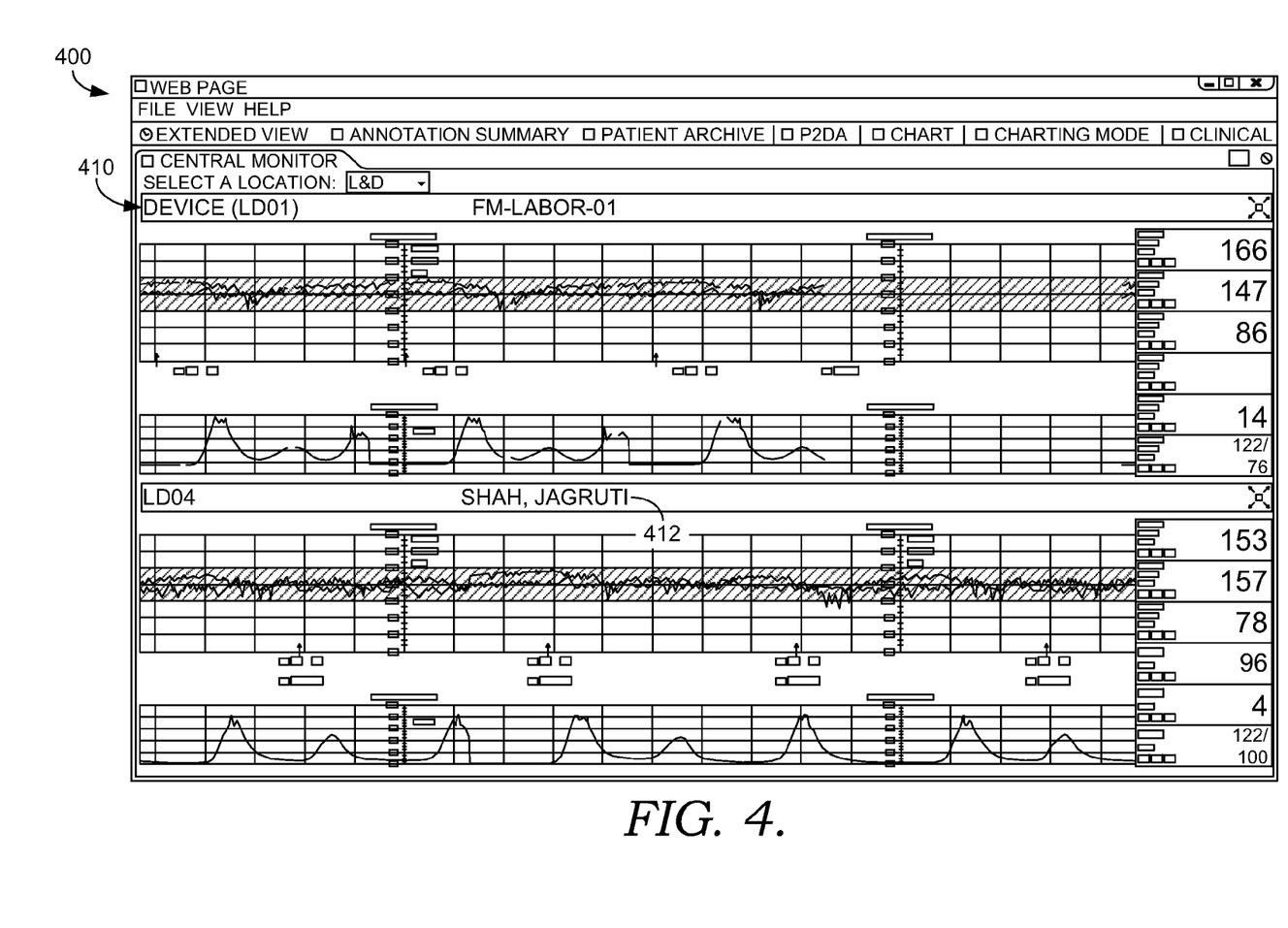

Turning now to FIG. 4, FIG. 4 illustrates a central monitor perspective 400 presenting two waveform tracing cells 410 and 412. The waveform tracing cell 410 is associated with an active monitoring device that has not been electronically associated with a patient. Because the monitoring device has not been electronically associated with a patient, only the device identifier is presented (LD01). The waveform tracing cell 412 is associated with a monitoring device that has been electronically associated with a patient (Jagruti Shah), and, thus, the patient's name is presented in conjunction with the waveform tracing. The waveform tracing cells 410 and 412 have associated vital signs display areas. Further, the waveform tracing cells 410 and 412 are presented in the predetermined aspect ratio.

Figure 5:
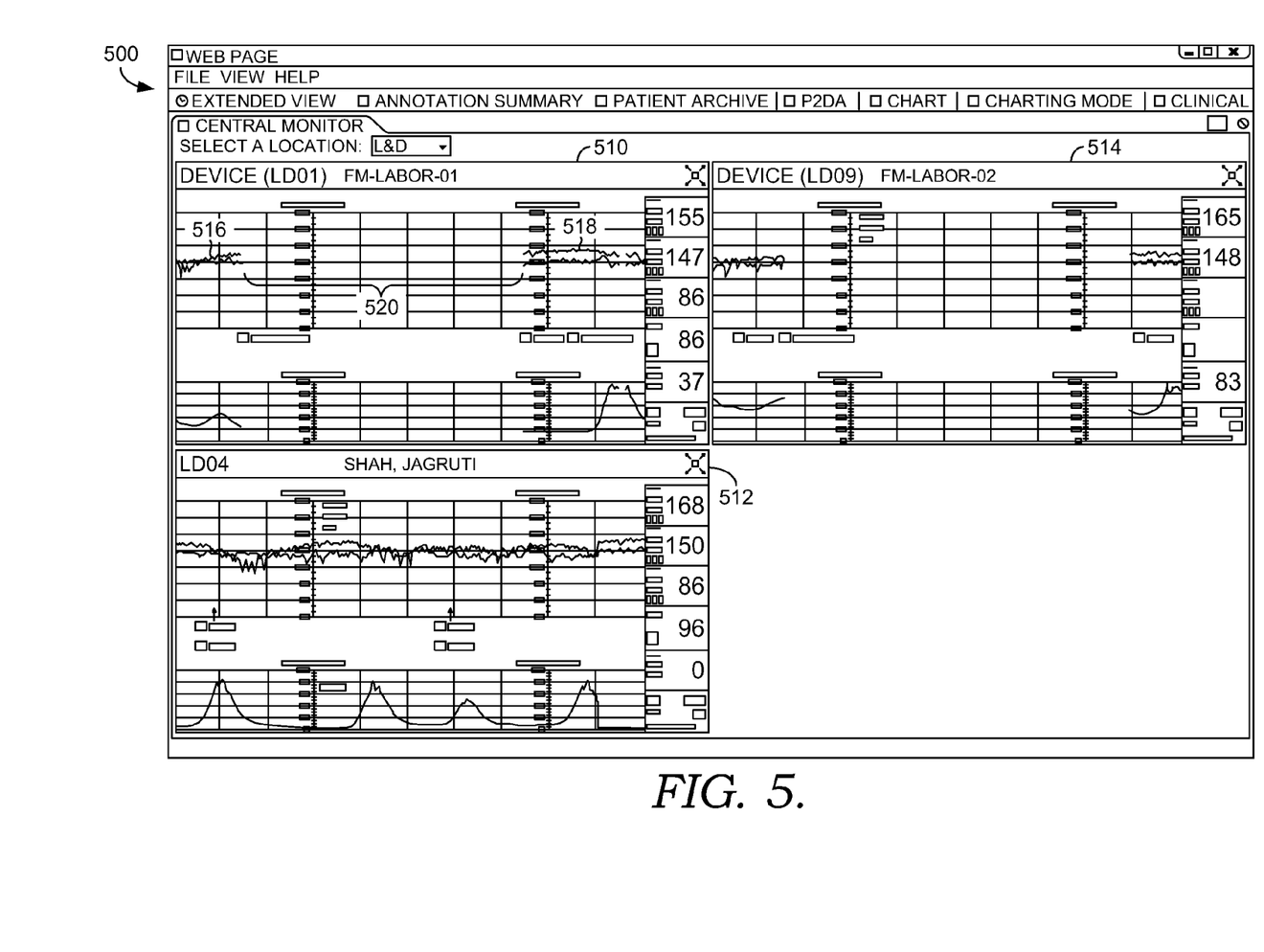

FIG. 5 illustrates a central monitor perspective 500 presenting three waveform tracing cells 510, 512, and 514 associated with three active monitoring devices. The waveform tracing cells 510, 512, and 514 share similarities with the waveform tracing cells discussed above. For brevity sake, these similarities will not be repeated here. As can be seen, the waveform tracing cells 510, 512, and 514 occupy substantially all of the central monitor perspective 500, but since there is an odd number of waveform tracing cells, a blank cell is presented in the central monitor perspective 500. Using the waveform tracing cell 510 as an example, waveform tracing information may include real-time waveform information 516 as well as historical waveform information 518. Waveform tracing information may also indicate when the monitoring device was disconnected from the patient (represented by interval 520).

Figure 6:
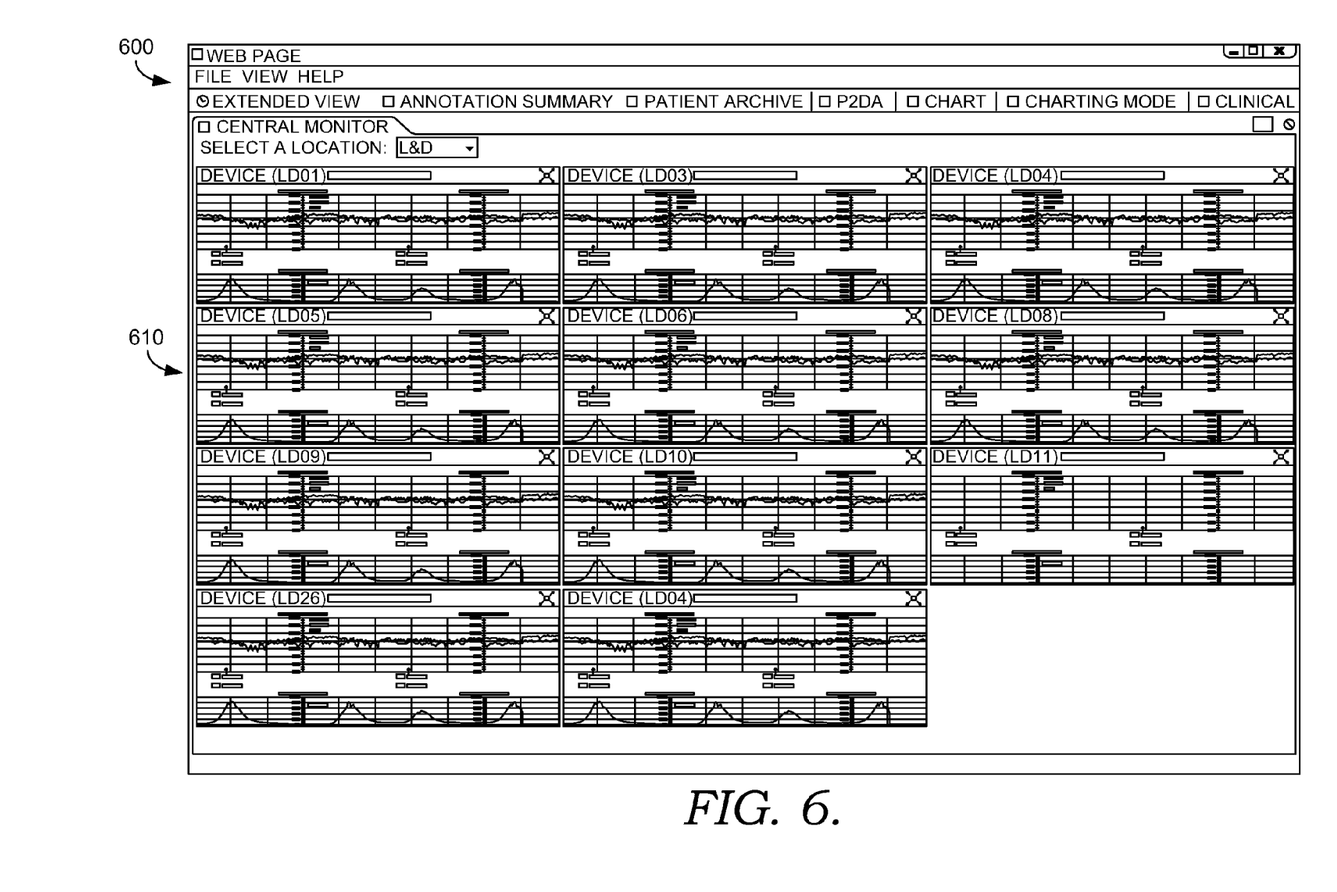

FIG. 6 illustrates a central monitor perspective 600 presenting eleven waveform tracing cells 610 (not individually numbered), all presented with the predetermined aspect ratio. To maximize the presentation of waveform information, the vital signs display area associated with each of the waveform tracings is no longer presented. This may occur, in one aspect, when nine or greater waveform tracing cells are presented. The eleven waveform tracing cells 610 represent active monitoring devices.

Figure 7:
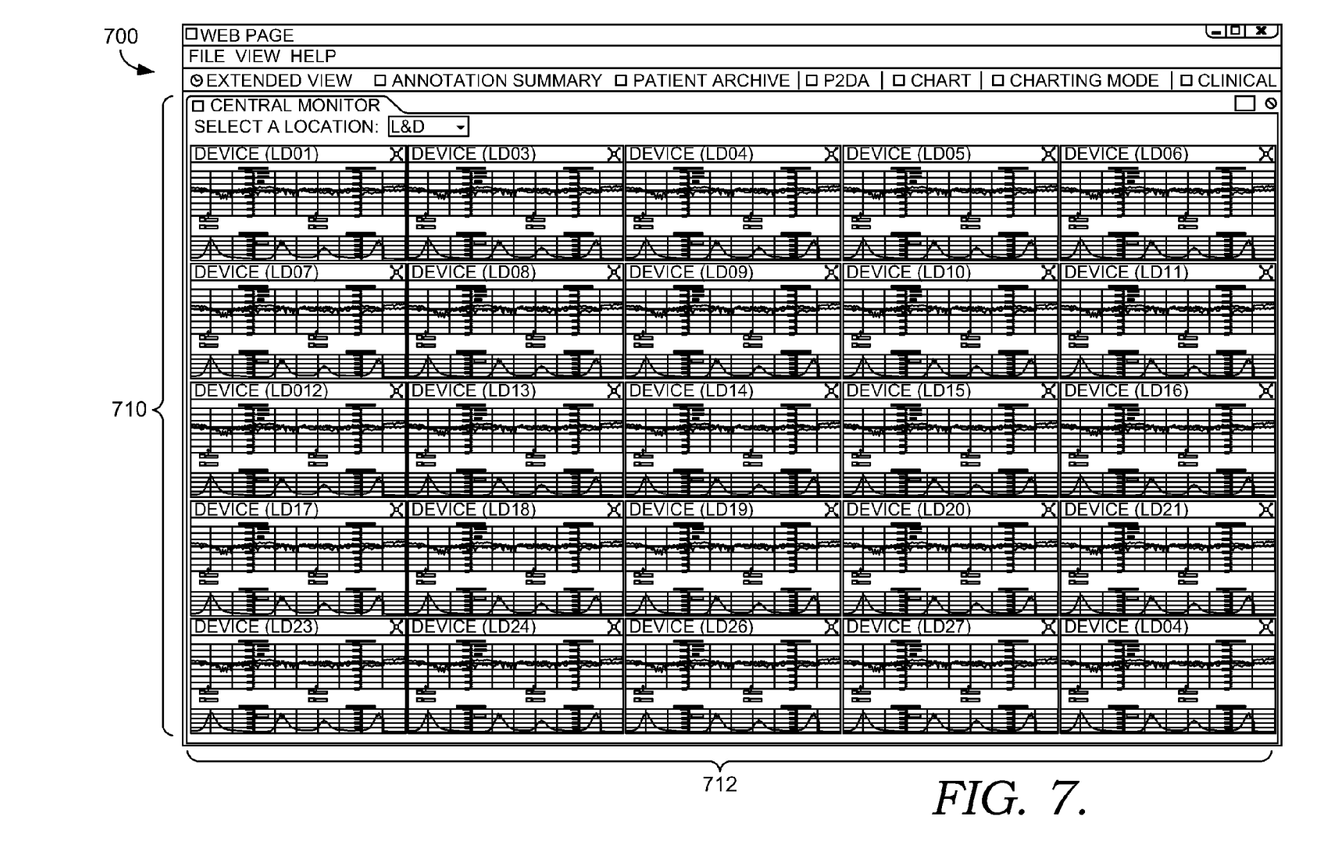

FIG. 7 illustrates a central monitor perspective 700 presenting a maximum of 25 waveform tracing cells (not individually numbered). The waveform tracing cells are arranged in a 5×5 grid and each are presented with the predetermined aspect ratio. In one aspect, if more than 25 monitoring devices with associated waveform tracings are detected, the excess waveform tracings may be presented on a second display device. If only one display device is available and there are more than 25 monitoring devices with associated waveform tracings detected, the user may be presented with a message informing him or her that more than 25 waveform tracings have been detected and to turn off any monitoring devices not in use. In this situation, the system may randomly select 25 different waveform tracings to display in the central monitor perspective. Further, the system may cycle through all the available waveform tracings so that each of the tracings is presented at some point in time. Any and all such aspects are contemplated as being within the scope of the invention.

FIGS. 3-7 provide examples of various configurations of waveform tracing cells. Other arrangements are contemplated with each arrangement of the cells occupying a substantial majority of the central monitor perspective and having the predetermined aspect ratio. Further, although FIGS. 3-7 depict 1, 2, 3, 11, and 25 waveform tracing cells respectively, it is contemplated that the central monitor perspective may present any number of waveform tracings between 1 and 25.

Figure 8:
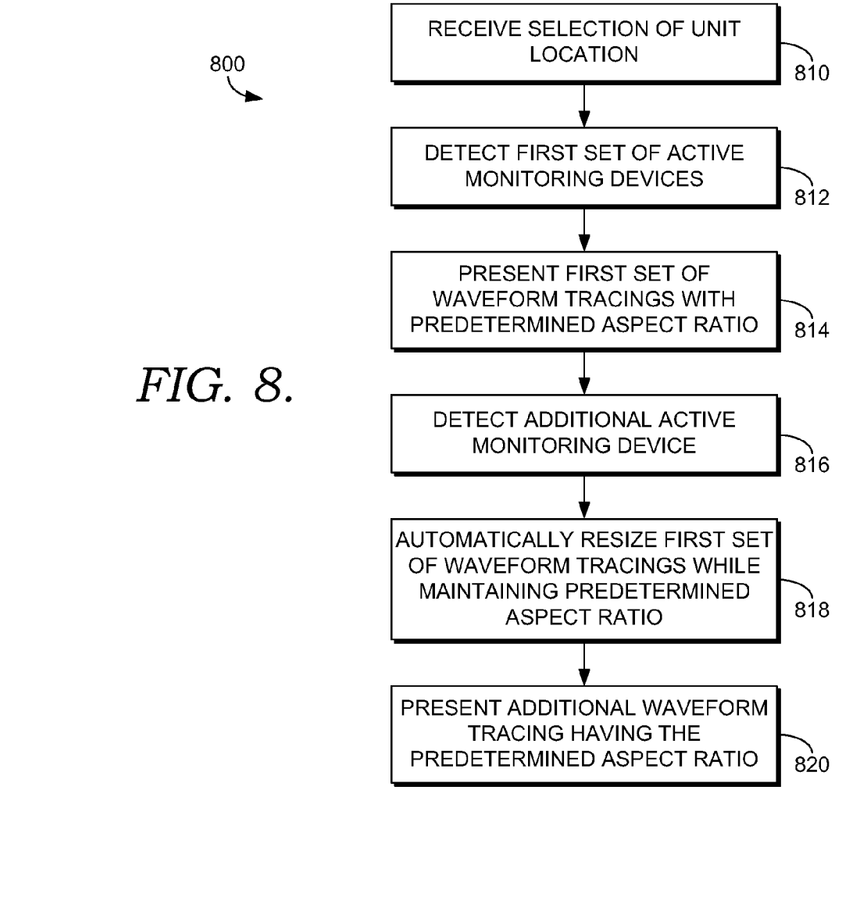
FIG. 8 is a flow diagram illustrating an exemplary method of automatically populating a central monitor perspective with waveform tracings in accordance with an embodiment of the present invention.

Turning now to FIG. 8, FIG. 8 depicts a flow diagram illustrating an exemplary method 800 of automatically populating a central monitor perspective with waveform tracings. The central monitor perspective may be associated with one display device or more than one display device. The display device(s) may be associated with a central location such as a nursing or clinician station associated with a unit at a healthcare facility. At a step 810, a selection of a unit location to present in the central monitor perspective is received by a receiving component such as the receiving component 218 of FIG. 2. The unit location may be associated with a healthcare facility and may include a labor and deliver unit, a telemetry unit, a unit that monitors electroencephalograms (EEGs), a pre- or post-surgical unit, an intensive care unit, or any other unit that monitors waveform tracing information.

At a step 812, a first set of monitoring devices that is connected to patients in the unit location is detected by a device detection component such as the device detection component 220 of FIG. 2. The device detection component may detect both monitoring devices that are electronically associated with patients and monitoring devices that are monitoring patients but have not been electronically associated with those patients.

At a step 814, a first set of waveform tracings associated with the first set of active monitoring devices is presented in the central monitor perspective by a rendering component such as the rendering component 222 of FIG. 2. Each waveform tracing of the first set of waveform tracings has a predetermined aspect ratio of approximately 1:24. Other aspect ratios contemplated include 1:20, 1:21, 1:22, and 1:23. The first set of waveform tracings may include uterine contraction waveform tracings and fetal heart rate waveform tracings. Other waveform tracings may include electrocardiogram tracings, EEG tracings, respiratory rate tracings, blood pressure tracings, maternal heart rate tracings, and the like.

Each waveform tracing of the first set of waveform tracings is presented in a separate cell. The cells are sized to substantially occupy the available screen real estate of the central monitor perspective. Further, each of the cells has approximately the same dimensions. The central monitor perspective is configured to present up to 25 separate cells.

At a step 816, and subsequent to presenting the first set of waveform tracings, an additional monitoring device that is monitoring a patient in the unit location is detected by, for example, the device detection component. The monitoring device is detected when it comes "online." The device detection component not only detects if the additional monitoring device is actively monitoring a patient but also detects if the additional monitoring device has been electronically associated with the patient. If the additional monitoring device has been electronically associated with the patient, the device detection component detects the patient's name and other identifying information.

At a step 818, the first set of waveform tracings is automatically resized while maintaining the predetermined aspect ratio. This may be accomplished by a resizing component such as the resizing component 224 of FIG. 2. A new waveform tracing associated with the additional monitoring device is simultaneously presented in the central monitor perspective at a step 820; the new waveform tracing is presented with the predetermined aspect ratio. The new waveform tracing is presented automatically and without human intervention. To accommodate the new waveform tracing, each waveform tracing of the first set of waveform tracings is resized downward.

The method 800 may further include detecting when a monitoring device is no longer connected to a patient and automatically removing a waveform tracing associated with the disconnected monitoring device from the central monitor perspective. Each of the remaining waveform tracings is simultaneously and automatically resized upward to substantially occupy the available screen real estate of the central monitor perspective.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. One or more non-transitory computer storage media having computer-executable instructions embodied thereon that, when executed, facilitate a method of automatically populating a central monitor perspective, the method comprising:
   receiving a selection of a unit location to present in the central monitor perspective;
   detecting a set of monitoring devices in the unit location;
   detecting a first monitoring device of the set of monitoring devices is online and actively monitoring a patient and has been associated with identification information of the patient;
   detecting that a second monitoring device of the set of monitoring devices is online and actively monitoring the patient or another patient but has not been associated with identification information of the patient or another patient;
   receiving output waveform tracing information from each of the first monitoring device that has been associated with identification information of the patient and the second monitoring device that has not been associated with identification information of the patient or another patient;
   presenting an initial set of waveform tracings comprising at least a first waveform tracing and a second waveform tracing respectively associated with the first monitoring device and the second monitoring device of the set of monitoring devices in the central monitor perspective, each waveform tracing of the initial set of waveform tracings having a predetermined aspect ratio, wherein the predetermined aspect ratio is a ratio between the x-axis and the y-axis;
   subsequent to presenting the initial set of waveform tracings in the central monitor perspective, detecting that an additional monitoring device is online in the unit location; and
   automatically presenting an additional waveform tracing associated with the additional monitoring device in the central monitor perspective, the first waveform tracing, the second waveform tracing, and the additional waveform tracing presented in a new set of waveform tracings, wherein each waveform tracing of the new set of waveform tracings is decreased in size as compared to each waveform tracing of the initial set of waveform tracings while maintaining the predetermined aspect ratio.

2. The media of claim 1, wherein each of the waveform tracings of the initial set of waveform tracings comprises at least one selected from the following:
   fetal heart rate waveform tracings, and
   maternal uterine contraction waveform tracings.

3. The media of claim 1, wherein the predetermined aspect ratio comprises a 1:24 ratio.

4. The media of claim 1, further comprising:
   detecting that at least one monitoring device is offline; and
   simultaneously and automatically removing a waveform tracing associated with the offline monitoring device and increasing in size the remaining waveform tracings while maintaining the predetermined aspect ratio.

5. The media of claim 1, wherein the central monitor perspective is presented on a single display device.

6. The media of claim 1, wherein the central monitor perspective is presented on more than one display device.

7. A computer system that facilitates automatically populating a central monitor perspective, the computer system comprising a processor coupled to a non-transitory computer storage medium, the computer storage medium having stored thereon a plurality of computer software components executable by the processor, the computer software components comprising:
a receiving component for receiving a selection of a unit location to display in the central monitor perspective;
a device detection component for automatically detecting at least two online monitoring devices in the unit location, the at least two online monitoring devices actively monitoring one or more patients, wherein at least a first of the at least two online monitoring devices has been associated with identification information of a patient of the one or more patients and at least a second of the at least two online monitoring devices has not been associated with identification information of the patient;
a rendering component for receiving output waveform tracing information from each monitoring device of the at least two online monitoring devices and presenting real-time waveform tracings associated with the at least two online monitoring devices in the central monitor perspective, the real-time waveform tracings having a predetermined aspect ratio, wherein the predetermined aspect ratio is a ratio between the x-axis and the y-axis; and
a resizing component for automatically decreasing a size of the real-time waveform tracings based on a number of the online monitoring devices, wherein the predetermined aspect ratio is maintained after decreasing the size of the real-time waveform tracings.

8. The system of claim 7, wherein the at least two monitoring devices comprise fetal monitoring devices.

9. The system of claim 7, wherein the device detection component further detects when at least one of the at least two monitoring devices is no longer online.

10. One or more non-transitory computer storage media having computer-executable instructions embodied thereon that, when executed, produce a graphical user interface (GUI) to facilitate automatically populating a central monitor perspective, the GUI comprising:
a location display area configured to present available unit locations in the central monitor perspective; and
a waveform tracing display area configured to present one or more waveform tracings associated with at least two online monitoring devices in the central monitor perspective, the at least two online monitoring devices actively monitoring one or more patients and configured to output waveform tracing information, wherein at least a first of the at least two online monitoring devices has been associated with identification information of a patient of the one or more patients and at least a second of the at least two online monitoring devices has not been electronically associated with identification information of the patient, and wherein:
(1) each waveform tracing of the one or more waveform tracings presented in a separate cell of the waveform tracing display area, wherein a total number of the occupied separate cells is configured to occupy the entire waveform tracing display area,
(2) each waveform tracing of the one or more waveform tracings having a same predetermined aspect ratio, wherein the same predetermined aspect ratio is a ratio between the x-axis and the y-axis, and
(3) each waveform tracing of the one or more waveform tracings is decreased in size based on displaying an additional waveform tracing from an additional online monitoring device, wherein the one or more waveform tracings decreased in size maintain the same predetermined aspect ratio.

11. The GUI of claim 10, further comprising:
a vital signs display area configured to display a vital signs perspective associated with a displayed waveform tracing.

12. The GUI of claim 10, further comprising a blank waveform tracing cell.

13. The media of claim 1, wherein the predetermined aspect ratio comprises at least one ratio selected from the following: 1:20, 1:21, 1:22, and 1:23.

14. The media of claim 1, further comprising determining a location of a monitoring device of the set of monitoring devices or a location of the additional monitoring device.

15. The system of claim 7, wherein the number of the online monitoring devices comprises the at least two online monitoring devices and at least one additional monitoring device that is included in the number of online monitoring devices when the at least one additional monitoring device changes from an offline state to an online state, and wherein the resizing component automatically decreases the size of the real-time waveform tracings based on the at least one additional monitoring device changing from the offline state to the online state.

16. The system of claim 15, wherein the device detection component automatically detects the at least one additional monitoring device when the at least one monitoring device changes from the offline to the online state.

17. The system of claim 7, wherein the at least two monitoring devices are detected by the device detection component when the at least two monitoring devices come online.

18. The system of claim 7, wherein the unit location comprises a labor and delivery nurse unit.

19. The GUI of claim 10, wherein the separate cells are arranged in a grid.

20. The GUI of claim 10, wherein the waveform tracing display area is further configured to present a patient name associated with at least one waveform tracing of the at least two waveform tracings, the at least one waveform tracing being associated with at least one monitoring device of the at least two monitoring devices.

* * * * *